United States Patent
Ravikumar et al.

(10) Patent No.: US 7,344,495 B2
(45) Date of Patent: Mar. 18, 2008

(54) SURGICAL RETRACTOR APPARATUS FOR USE WITH A SURGICAL PORT

(75) Inventors: Sundaram Ravikumar, Briarcliff Manor, NY (US); Mark Peyser, Easton, CT (US)

(73) Assignee: Arvik Enterprises, LLC, Dobbs Ferry, NY (US)

( * ) Notice: Subject to any disclaimer, the term of this patent is extended or adjusted under 35 U.S.C. 154(b) by 0 days.

(21) Appl. No.: 11/122,846

(22) Filed: May 5, 2005

(65) Prior Publication Data
US 2005/0215863 A1    Sep. 29, 2005

Related U.S. Application Data

(63) Continuation-in-part of application No. 10/766,597, filed on Jan. 27, 2004, now Pat. No. 7,195,592.

(51) Int. Cl.
*A61B 1/32* (2006.01)
(52) U.S. Cl. .................. 600/219; 600/224; 600/233
(58) Field of Classification Search .............. 600/204, 600/208, 214–215, 219, 222, 224, 231, 233–234, 600/210; 604/104; 606/198
See application file for complete search history.

(56) References Cited

U.S. PATENT DOCUMENTS

| | | | |
|---|---|---|---|
| 1,020,281 A * | 3/1912 | Hall ........................... 600/224 |
| 2,083,573 A * | 6/1937 | Morgan ...................... 600/224 |
| 2,548,602 A | 4/1951 | Greenburg |
| 3,044,461 A | 7/1962 | Murdock |
| 4,130,113 A * | 12/1978 | Graham ...................... 600/224 |
| 4,424,724 A | 1/1984 | Bookwalter et al. |
| 4,716,901 A | 1/1988 | Jackson et al. |
| 4,899,729 A | 2/1990 | Gill et al. |
| 5,052,373 A | 10/1991 | Michelson |
| 5,176,659 A | 1/1993 | Mancini |
| 5,183,464 A | 2/1993 | Dubrul et al. |
| 5,197,971 A | 3/1993 | Bonutti |
| 5,232,451 A | 8/1993 | Freitas et al. |
| 5,312,360 A | 5/1994 | Behl |
| 5,370,134 A | 12/1994 | Chin et al. |
| 5,377,667 A * | 1/1995 | Patton et al. ............... 600/184 |
| 5,431,676 A | 7/1995 | Dubrul et al. |
| 5,441,486 A | 8/1995 | Yoon |
| 5,460,170 A | 10/1995 | Hammerslag |
| 5,503,617 A | 4/1996 | Jako |
| 5,520,610 A | 5/1996 | Giglio et al. |
| 5,667,481 A | 9/1997 | Villalta et al. |
| 5,674,240 A | 10/1997 | Bonutti et al. |
| 5,688,223 A | 11/1997 | Rosendahl |
| 5,728,046 A | 3/1998 | Mayer et al. |
| 5,795,289 A | 8/1998 | Wyttenbach |

(Continued)

*Primary Examiner*—Cary E. O'Connor
(74) *Attorney, Agent, or Firm*—Gordon & Jacobson, PC

(57) ABSTRACT

An improved surgical retraction apparatus (and corresponding method of operation) includes a plurality of rigid retraction members disposed about a central axis that move radially with respect to the central axis between a closed state and an open state. In the closed state, the retraction members form a central opening that is adapted to closely fit around the tubular section of a surgical port device. In the illustrative embodiment, a planetary gear train, cable assemblies, lever arms or two annular slotted plates used to control radial movement of the retraction members with respect to the central axis.

2 Claims, 10 Drawing Sheets

U.S. PATENT DOCUMENTS

| | | |
|---|---|---|
| 5,813,978 A | 9/1998 | Jako |
| 5,827,319 A | 10/1998 | Carlson et al. |
| 5,928,139 A | 7/1999 | Koros et al. |
| 5,944,658 A | 8/1999 | Koros et al. |
| 5,957,902 A | 9/1999 | Teves |
| 5,967,891 A | 10/1999 | Riley et al. |
| 5,967,970 A | 10/1999 | Cowan et al. |
| 5,967,972 A | 10/1999 | Santilli et al. |
| 6,080,174 A | 6/2000 | Dubrul et al. |
| 6,083,154 A | 7/2000 | Liu et al. |
| 6,159,179 A | 12/2000 | Simonson |
| 6,224,608 B1 | 5/2001 | Ciccolella et al. |
| 6,228,068 B1 | 5/2001 | Yoon |
| 6,245,052 B1 | 6/2001 | Orth et al. |
| 6,277,094 B1 | 8/2001 | Schendel |
| 6,325,812 B1 | 12/2001 | Dubrul et al. |
| 6,354,995 B1 * | 3/2002 | Hoftman et al. ............ 600/219 |
| 6,358,266 B1 | 3/2002 | Bonutti |
| 6,440,063 B1 | 8/2002 | Beane et al. |
| 6,464,634 B1 | 10/2002 | Fraser |
| 6,616,678 B2 | 9/2003 | Nishtala et al. |
| 6,626,859 B2 | 9/2003 | Von Segesser |
| 6,706,017 B1 | 3/2004 | Dulguerov |
| 6,712,795 B1 | 3/2004 | Cohen |
| 2004/0087833 A1 | 5/2004 | Bauer et al. |
| 2005/0159650 A1 | 7/2005 | Raymond et al. |
| 2005/0203347 A1 * | 9/2005 | Fehling ...................... 600/210 |

* cited by examiner

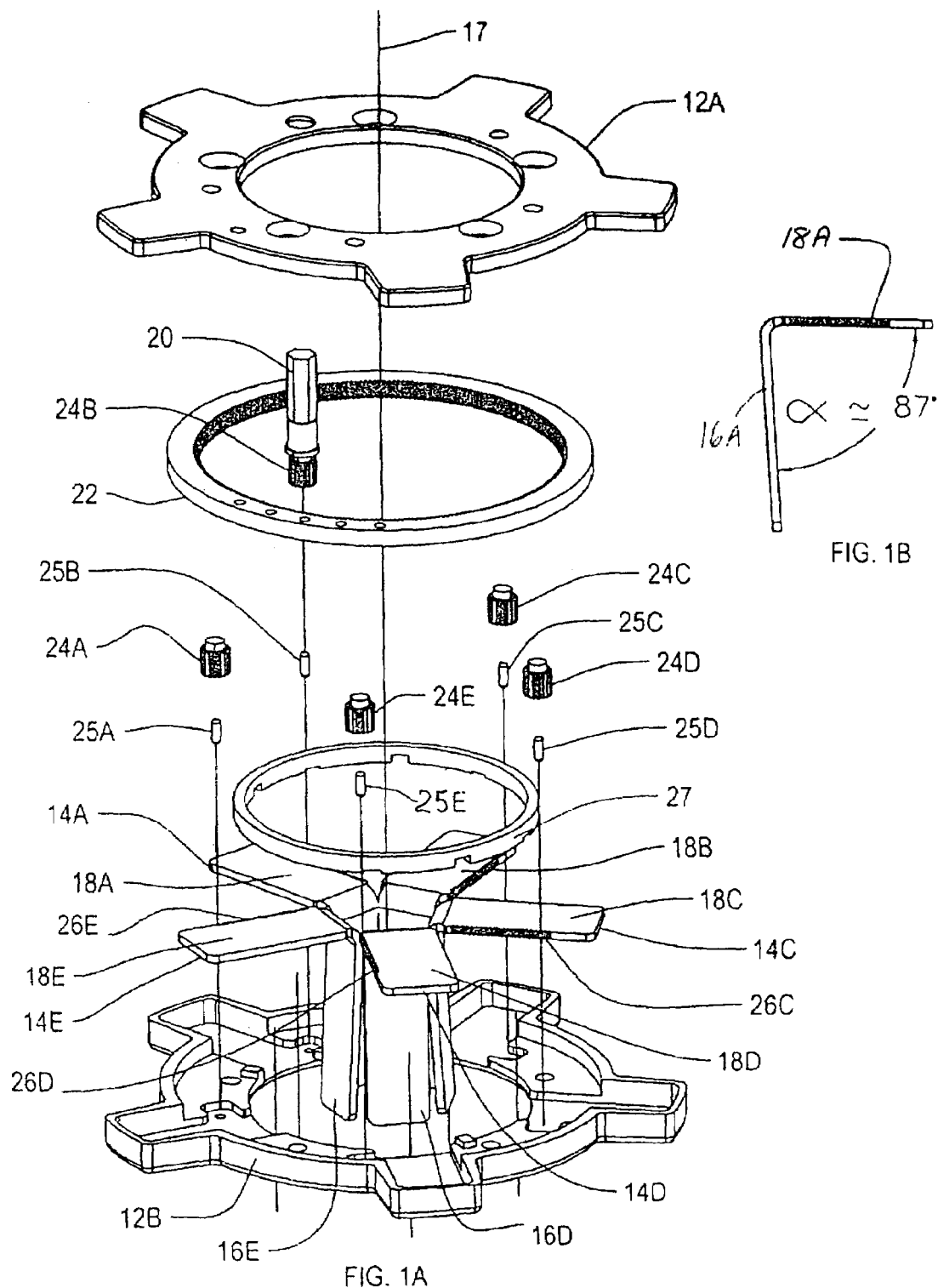

SURGICAL RETRACTOR APPARATUS FOR USE WITH A SURGICAL PORT

CROSS-REFERENCE TO RELATED APPLICATIONS

The present application is a continuation-in-part of U.S. patent application Ser. No. 10/766,597, filed on Jan. 27, 2004 now U.S. Pat. No. 7,195,592, commonly assigned to assignee of the present invention, herein incorporated by reference in its entirety.

BACKGROUND OF THE INVENTION

1. Field of the Invention

This invention relates broadly to surgical instruments. More particularly, this invention relates to a retraction apparatus for use with a surgical port device. In addition, the invention relates to an improved methodology for performing retraction of the tissue surrounding a surgical port device.

2. State of the Art

Laparoscopic (Thoracoscopic) surgical procedures are facilitated by the use of surgical ports (commonly referred to as "trocars") that provide access into the abdominal cavity (thoracic cavity). Various surgical instruments (e.g., imaging probes, cutting blades, clamps/suturing devices, etc.) are inserted into the abdominal cavity (thoracic cavity) via such ports and are manipulated in the cavity. Typically, such surgical ports employ a cannula as the passageway for the various instruments. Often, internal pressures in the body cavity are elevated by insufflation via an external pressure source operably coupled to the body cavity through an inlet in the surgical port. In such configurations, the surgical ports often employ gaskets disposed upstream from the inlet that maintain the elevated internal pressures in the body cavity while inserting/removing instruments through the cannula of the port.

In many laparoscopic/thoracoscopic surgical procedures, it is desirable at some point in the procedure to provide the surgeon with a relatively large size opening into the body. The large size opening enables the surgeon to use larger surgical instruments. It also enables visualization of the surgical site without a camera. Finally, the large size opening enables the removal of larger organs (or pieces of such large organs) through the body wall in less time.

Various surgical retractors have been developed to assist surgeons in retracting tissue surrounding an incision into the body wall. One common configuration for surgical retractors is to mount a plurality of retractors to a circular support ring. An example of such a configuration is shown in U.S. Pat. No. 5,688,223. However, this configuration is unsuitable for use with a surgical port device because its nested configuration (when closed) will not fit around a surgical port device. Moreover, the radial position of the arms of the retractor are manually adjusted individually, which is cumbersome and time-consuming.

Thus, there remains a need in the art for improved surgical retraction devices that are suitable for use with surgical ports and thus overcome the limitations provided by these prior art retraction devices.

SUMMARY OF THE INVENTION

It is therefore an object of the invention to provide a surgical retraction device (and corresponding method of operation) that is suitable for use with a surgical port device.

It is another object of the invention to provide a surgical retraction device (and corresponding method of operation) that quickly and effectively forms an opening of variable size through a body wall.

It is a further object of the invention to provide a surgical retraction device wherein the user can easily adjust the size of the opening through the body wall.

It is also an object of the invention to provide a surgical retraction device suitable for use in a broad range of laparoscopic and thoracoscopic surgical procedures.

In accord with these objects, which will be discussed in detail below, an improved surgical retraction apparatus is provided. The apparatus has a plurality of rigid retraction members disposed about a central axis that move radially with respect to the central axis between a closed state and an open state. In the closed state, the retraction members form a central opening that is adapted to closely fit around the tubular section of a surgical port device. In the illustrative embodiments, a planetary gear train, cable assemblies, lever arms, and slotted plates may be used to control radial movement of the retraction members with respect to the central axis.

It will be appreciated that the radial position of the retraction members of the surgical retraction apparatus are easily adjusted to provide a wide range of opening sizes into the body, and thus are effective in retracting tissue for many different surgical applications. In addition, the surgical retraction apparatus of the present invention is simple to use and effective in conjunction with surgical port devices, and thus is effective in a wide range of laparoscopic and thoracoscopic procedures.

Additional objects and advantages of the invention will become apparent to those skilled in the art upon reference to the detailed description taken in conjunction with the provided figures.

BRIEF DESCRIPTION OF THE DRAWINGS

FIG. 1A is an exploded view of a surgical retraction apparatus in accordance with the present invention.

FIG. 1B is a partial side view of one of the retraction arms of FIG. 1A in accordance with the present invention.

DETAILED DESCRIPTION OF THE PREFERRED EMBODIMENTS

Figure 2A:
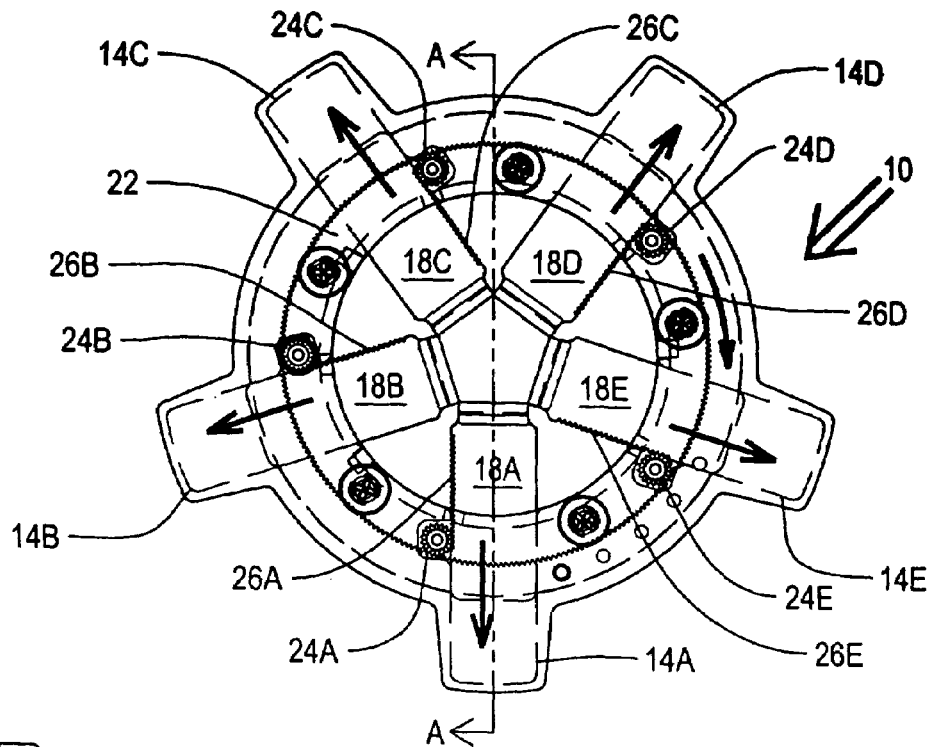
FIGS. 2A-2C illustrate the surgical retraction apparatus of FIG. 1 in its non-retracted "closed" configuration.

As used herein, the term "distal" is generally defined as in the direction of the patient and pertinent body cavity, or away from a user of the device (e.g., a doctor). Conversely, "proximal" generally means in the direction away from the patient/pertinent body cavity, or toward the user of the device.

Turning now to FIGS. 1, 2A-2C, 3A-3C, there is shown an improved surgical retraction apparatus in accordance with the present invention. The surgical retraction apparatus 10 includes a two-part housing (housing elements 12A, 12B) that supports a plurality of retraction members (for example, the five labeled 14A, 14B, 14C, 14D and 14E). The retraction members are generally L-shaped, with each having an arm (16A, 16B, 16C, 16D, 16E) that projects along a direction substantially parallel to a central axis 17 and a segment (18A, 18B, 18C, 18D, 18E) that projects radially outward from its arm. In order to the provide a bias force that maintains the arms in position against body tissue, the arms may be angled away from normal (for example, on the order of 87 degrees) as shown in FIG. 1B. The arms (16A, 16B, 16C, 16D, 16E) are translated in the radial direction (perpendicular to the central axis 17) by a planetary gear train. The planetary gear train includes a sun gear 22 and a plurality of planetary pinion gears 24A, 24B, 24C, 24D, 24E that mesh to the inner diameter teethed surface of the sun gear 22. The pinion gears 24A, 24B, 24C, 24D, 24E also mesh with the corresponding teethed surface 26A, 26B, 26C, 26D, 26E of the segments 18A, 18B, 18C, 18D, 18E to form a rack and pinion interface for each retraction member. A spline 20 is integral to one of the planetary gears (for example, planetary gear 24B as shown). A handle or knob (not shown) is attached to the spline 20. User rotation of the handle or knob drives the spline 20 and planetary pinion gear 24B, which acts as a drive gear to drive rotation of the sun gear 22. Pins 25A, 25B, 25C, 25D, 25E and a ring spacer 27 may be used to hold the planetary gears in place (meshed) against the inner diameter teethed surface of the sun gear 22 as shown. In this configuration, user rotation of the handle or knob in the clockwise direction causes the drive planetary pinion gear 24B to rotate in the clockwise direction, which causes the sun gear 22 to rotate in the clockwise direction. The clockwise rotation of the sun gear 22 causes the other planetary pinion gears 24A, 24C, 24D, 24E to rotate in the clockwise direction. The clockwise rotation of the pinion gears causes translation of the rack surfaces 26A, 26B, 26C, 26D, 26E in the radial direction away from the central axis. Similarly, the rotation of the or knob and drive planetary pinion gear in the counter-clockwise direction causes the sun gear 22 to rotate in the counter-clockwise direction, which causes the other planetary pinion gears 24A, 24C, 24D, 24E to rotate in the counter-clockwise direction. The counter-clockwise rotation of the planetary pinion gears causes translation of the rack surfaces 26A, 26B, 26C, 26D, 26E in the radial direction toward the central axis. In this manner, rotation of the handle or knob and drive planetary pinion gear effectuates retraction of the arms 16A, 16B, 16C, 16D, 16E in the radial direction away from (and towards) the central axis 17.

Figure 2B:
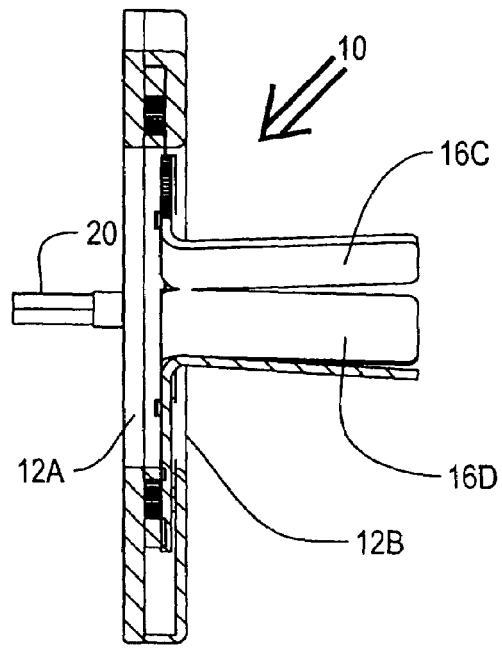
Figure 2C:
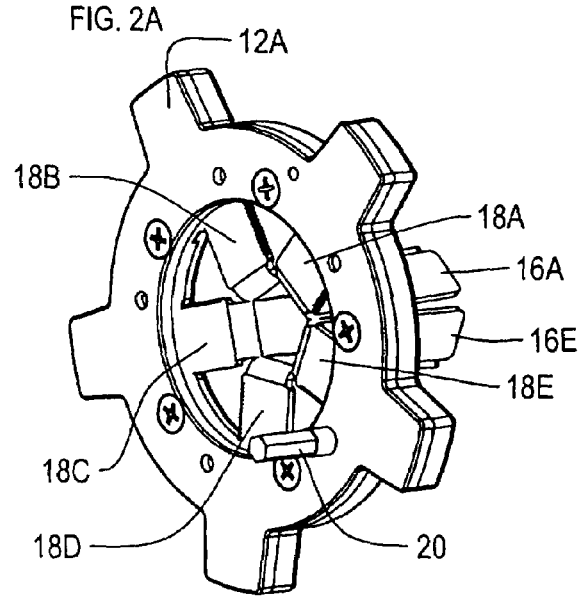

FIGS. 2A-2C illustrate the surgical retraction apparatus of FIG. 1 in its non-retracted "closed" configuration. FIG. 2B is a cross-sectional view across line A-A in FIG. 2A. In this configuration, the retraction arms 16A, 16B, 16C, 16D, 16E form a substantially-closed tube-shaped structure about the central axis 17 as best shown in FIG. 2C. Moreover, it is contemplated that the outside surfaces of the retraction arms 16A, 16B, 16C, 16D, 16E may include projections (not shown) that form a screw thread surface about the outside diameter of such tube-shape structure. The screw thread surface can be used to screw the retraction apparatus into place against the body wall and retain it in its desired position against the body wall during retraction.

Figure 3A:
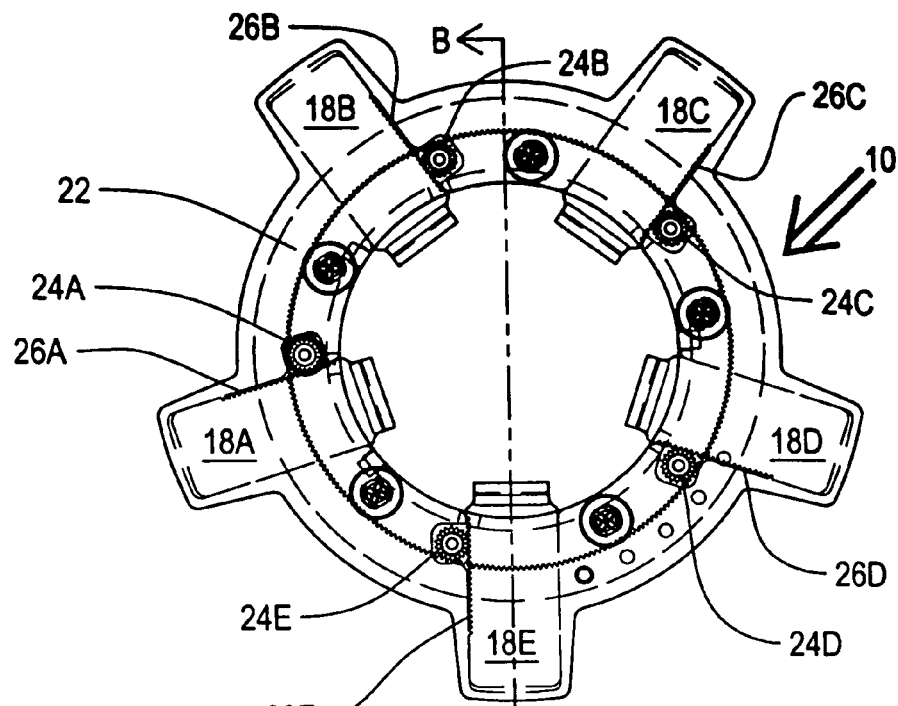
FIGS. 3A-3C illustrate the surgical retraction apparatus of FIG. 1 in its fully-retracted "open" configuration.
Figure 3B:
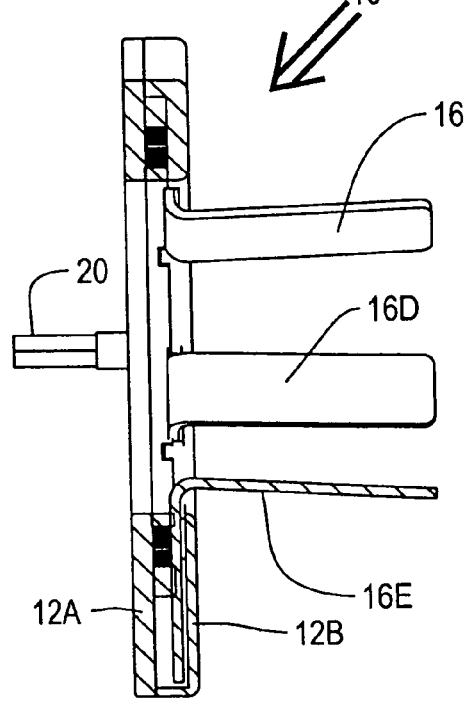
Figure 3C:
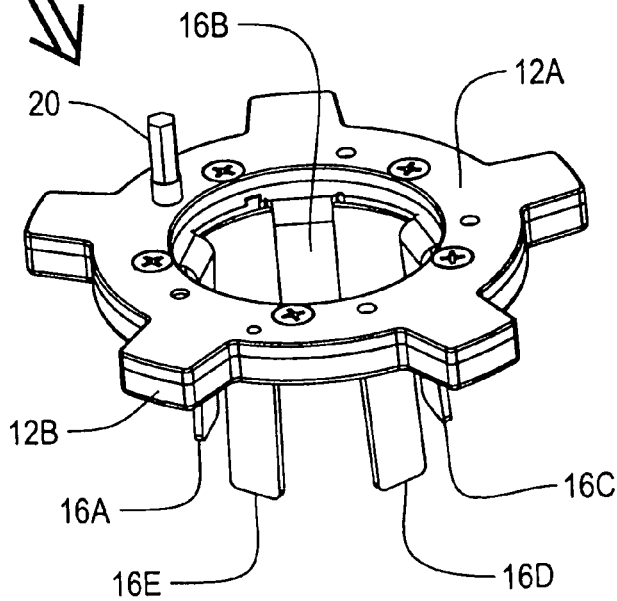

FIGS. 3A-3C illustrate the surgical retraction apparatus of FIG. 1 in its fully-retracted "open" configuration. FIG. 3B is a cross-sectional view across line B-B in FIG. 3A. In this configuration, the retraction arms 16A, 16B, 16C, 16D, 16E are radially disposed about the central axis 17 to form pieces of a broken tube-shaped structure as best shown in FIG. 2C. As is evident, the diameter of the broken-tube shaped structure formed by the retractor arms in the "open" configuration is significantly larger than the diameter of the tube-shaped structure formed by the retractor arms in the "closed" configuration.

Figure 4A:
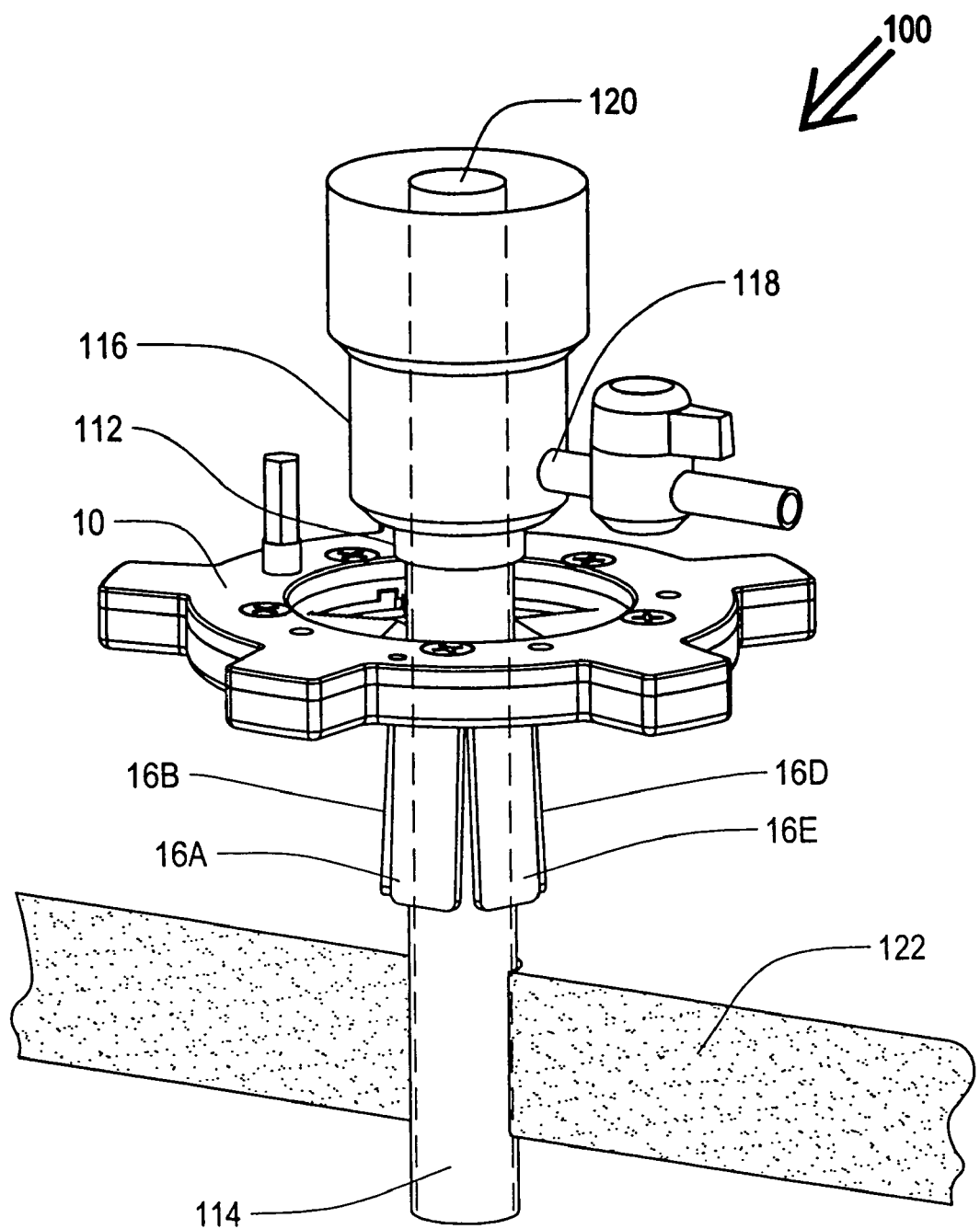
FIG. 4A is a view of the surgical retraction apparatus of FIG. 1 mounted onto the tubular section of a surgical port body that is inserted through the body wall of a patient during surgery.
Figure 4B:
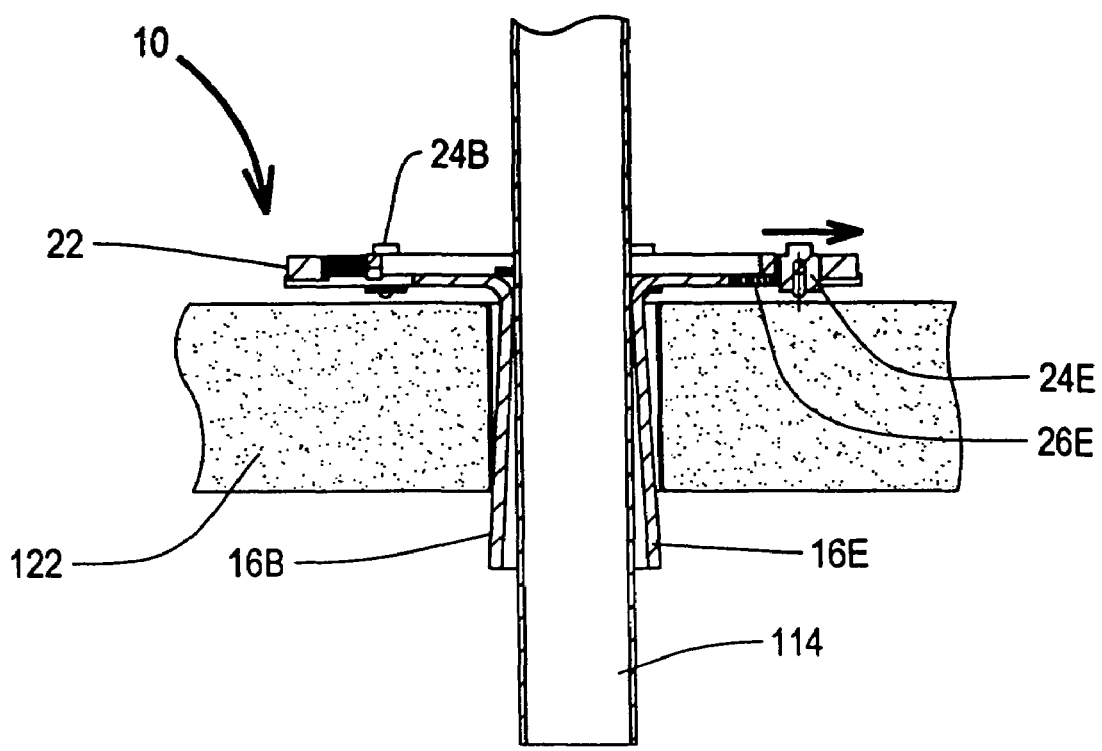
FIG. 4B is a diagrammatic view illustrating the insertion of the surgical retraction apparatus of FIG. 1 into regions between the tubular section of the port body and the body wall.
Figure 4C:
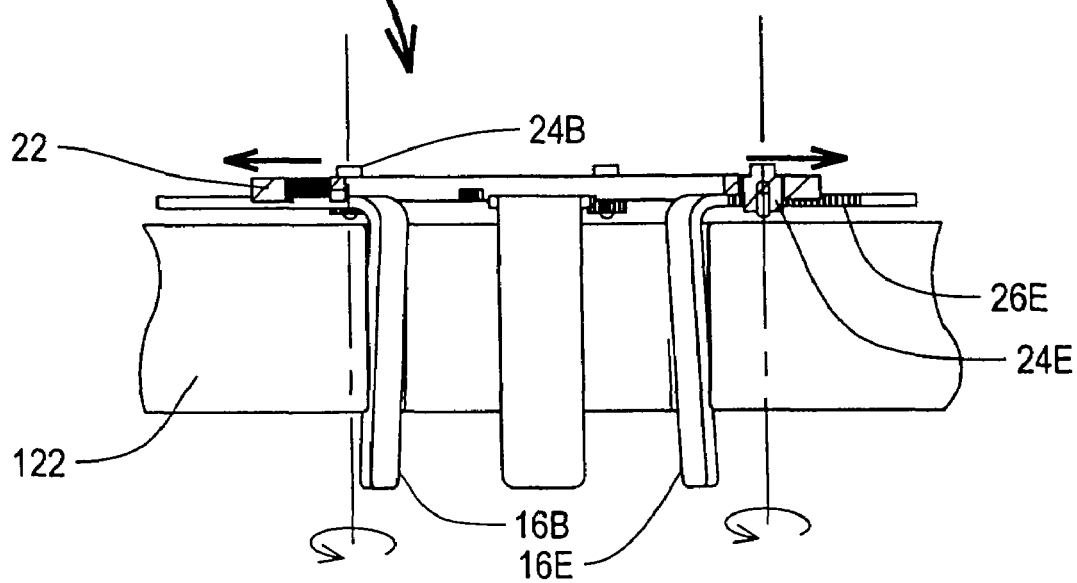
FIG. 4C is a diagrammatic view illustrating the retraction of the body wall by the retraction members of the surgical retraction apparatus of FIG. 1, with the port body removed from the large size opening created by such retraction.

Turning now to FIGS. 4A, 4B and 4C, there is shown an improved surgical port device 100 in accordance with the present invention, including a port body 112 with a rigid tubular section 114 and a side port section 116 disposed at the proximal end of the tubular section 114. The side port section 116 includes a side port 118 that is in fluid communication with a passageway 120 leading through the tubular section 114. The side port 118 is used for insufflation via an external pressure source operably coupled through the side port. In addition, the port body 112 includes a valve assembly (not shown) disposed at the proximal end of the port body 112 that maintains the elevated internal pressures in the body cavity during insufflation while inserting/removing instruments through the passageway 120 of the port body 112. The side port 118 may also be used for flushing as well. It should be appreciated that the side port section 116 may be omitted from the port body 112 while maintaining the valve assembly.

The surgical retraction apparatus 10 of FIG. 1 is adapted such that the diameter of the tube shaped structure formed by the retractor arms in the "closed" configuration fits closely to the outer diameter surface of the tubular section 114. The surgical retraction device 10 is positioned in its "closed" configuration over the tubular section 114 as shown in FIG. 4A.

As described above, the port body 112 defines a passageway 120 through which surgical instruments are inserted and manipulated during surgical operations performed with the port device secured in place to the body wall. In order to secure the port device to the body wall of a patient, a sharp trocar assembly (which includes the port body) may be utilized to puncture the skin and body wall or an incision may be made into the skin at the desired entry site for the port device and an obturator (not shown) may be inserted into the passageway 120 of the port body 112 such that its tip extends from the distal end of the tubular section 114. The sharp trocar assembly (or the obturator and port body) are pushed through a narrow opening in the body wall at the entrance site. The sharp trocar assembly (or obturator) is then removed from the port body 112 such that tubular section 114 remains in the body wall 122 as shown in FIG. 4A.

After inserting the port body 112 through the body wall 122, irrigation of the entry site may be performed, if necessary. Surgical instruments (e.g., laparoscopic instruments, cutting blades, clamps/suturing devices, imaging probes, etc.) may then be inserted (and manipulated) into the body cavity through the passageway 120 provided by the port body 112 and the tubular section 114. During use, the orientation of the port body 112 may be manipulated such that it is angled with respect to the orientation of the narrow opening in the body wall at the entrance site. During such use, the body wall 122 exerts forces upon the port body 122. Preferably, the tubular section 114 is made of rigid material (for example, stainless steel, rigid plastic such as liquid crystal polymer or polycarbonate, glass-filled polycarbonate, or the like) such that the port body 112 does not substantially deform in response to such forces, thereby enabling the tubular structure of passageway 120 to substantially remain unchanged. In this manner, the orientation of the port body 112 may be angled via manipulation of the port body 112 without interfering with insertion, removal or other user manipulation of a medical instrument passing the passageway 120. This enables the medical instrument to freely move through the tubular section 114 while the orientation of the port body 112 is angled via manipulation.

When the tubular section 114 of the port device 100 is initially inserted into the body wall, the retraction apparatus 10 may be positioned such that the retraction arms 16A, 16B, 16C, 16D, 16E engage the body wall 122. Alternatively, it may be positioned proximal to the body wall 122, such that when retraction is desired, force is applied to the retraction apparatus 10 along the distal direction such that the retraction arms 16A, 16B, 16C, 16D, 16E engage the body wall 122. In either case, the retraction arms 16A, 16B, 16C, 16D, 16E are inserted into regions between the tubular section 114 and the body wall 122 as best shown in FIG. 4B. The user then rotates the handle or knob to retract the arms 16A, 16B, 16C, 16D, 16E in the radial direction away from the central axis 17 of 14 the retraction apparatus as described above. The retraction of the retraction arms retracts the body wall 122 away from the tubular section 114 and increases the size opening into the body wall. The tubular section 114 (along with the port body 112) is then easily removed from the body wall 122 by lifting in the proximal direction, thereby leaving the large size opening in the body wall that is supported by the retraction arms of the retraction apparatus 10 as shown in FIG. 4C. Advantageously, the large size opening afforded by the retraction apparatus 10 enables the use of larger surgical instruments, enables visualization of the surgical site without a camera, and also enables the expeditious removal of larger organs (or pieces of such large organs) through the body wall 122.

With the port body 112 removed, the retractor apparatus 10 is preferably free-floating in the incision through the body wall. The retractor apparatus 10 may also be used in conjunction with a support apparatus (not shown) that retains the retractor apparatus 10 in a stationary position over the patient.

When retraction of the body wall 122 is no longer necessary, the user preferably rotates the handle or knob of the retractor apparatus 10 to retract the arms 16A, 16B, 16C, 16D, 16E in the radial direction towards the central axis (and preferably to its closed configuration as described above with respect to FIGS. 2A, 2B and 2C). The retraction apparatus 10 may be removed from the body wall 122 by applying a lifting force in the proximal direction. Alternatively, the tubular section 114 of the port body 112 may be re-inserted into the tubular-shaped structure formed by the arms 16A, 16B, 16C, 16D, 16E of the retraction apparatus 10 to continue the procedure using the port device. In any event, when the surgical procedure is finished, both the retraction apparatus 10 and the port body 112 are removed from the body wall 122 and the incision site is closed by conventional methods (such as stitching or stapling) or other desired methods.

Figure 5A:
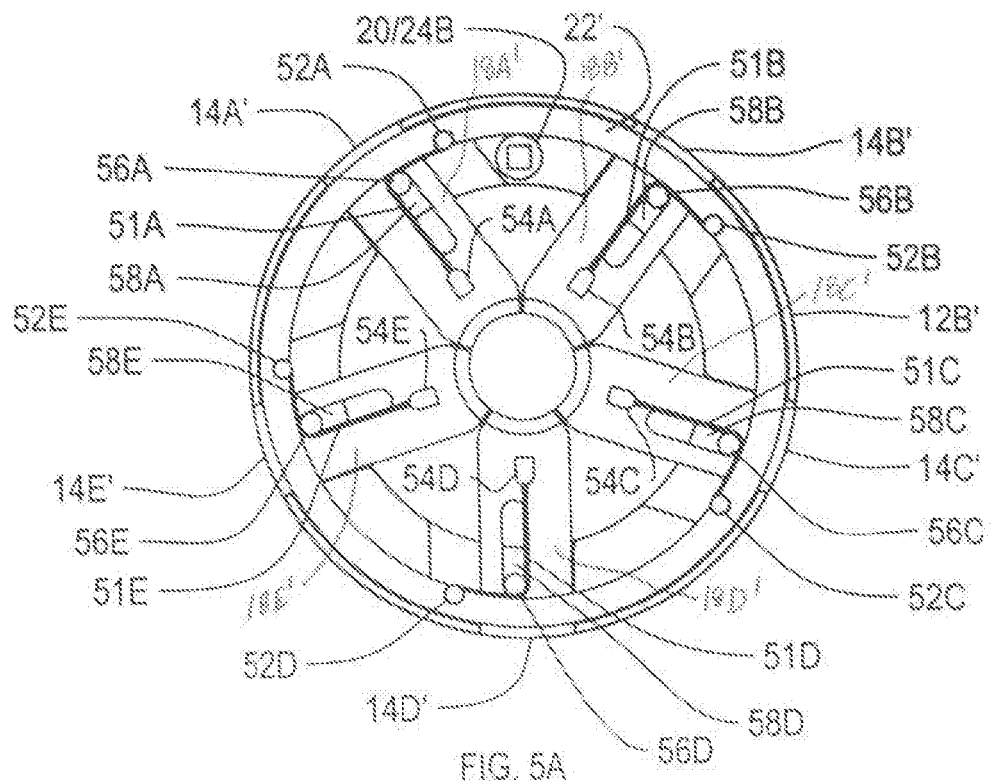
FIGS. 5A and 5B are schematic views illustrating an alternate embodiment of a surgical retraction apparatus according to the present invention wherein radial movement of the retraction members of the surgical retraction apparatus are effectuated with a cable and pulley mechanisms; the surgical retraction apparatus of FIG. 5A is in its non-retracted "closed" configuration; the surgical retraction apparatus of FIG. 5B is in its fully-retracted "open" configuration.
Figure 5B:
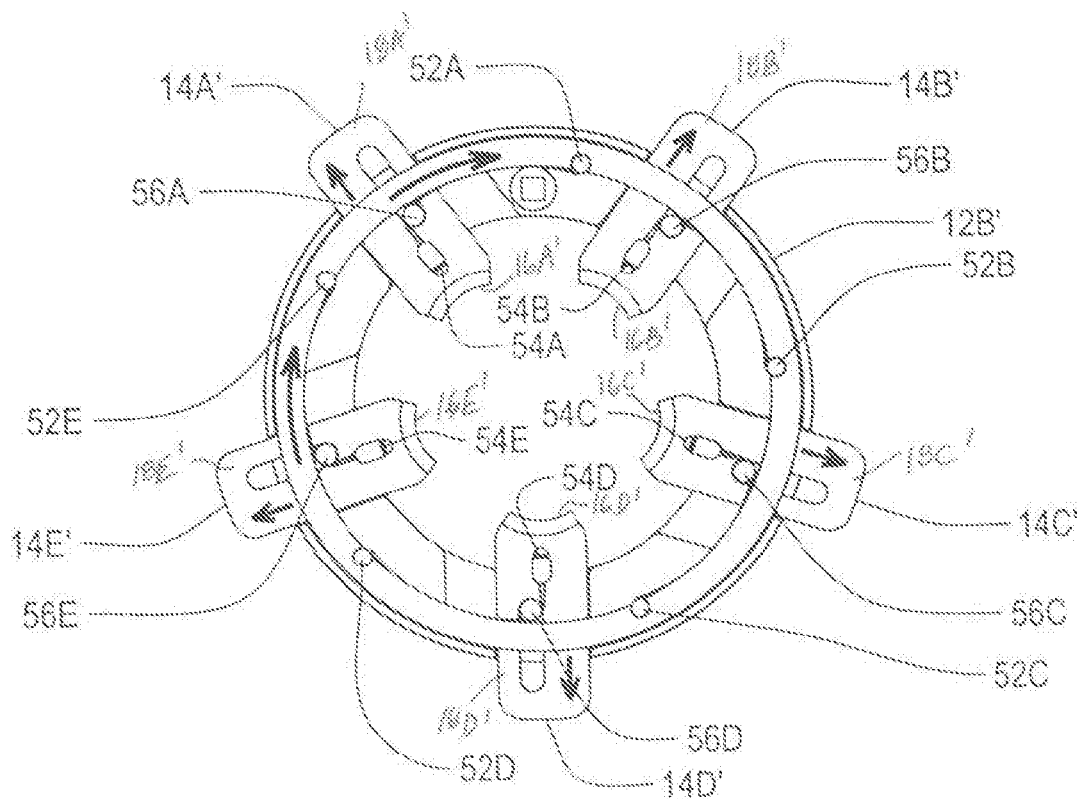

A second embodiment of a surgical retraction apparatus according to the present invention is shown in FIGS. 5A and 5B. In this second embodiment, the rack and pinion interfaces of the apparatus of FIGS. 1-3C are substituted with cable assemblies mounted within the housing (e.g., housing part 12B'). The cable assemblies are pulled around stationary posts to effectuate retraction of the retraction members. As shown, the cable assemblies include cables 51A, 51B, 51C, 51D, 51E whose ends are fixable attached to respective first connectors 52A, 52B, 52C, 52D, 52E and second connectors 54A, 54B, 54C, 54D, 54E. The first connectors 52A, 52B, 52C, 52D, 52E are mounted about the circumference of the sun gear 22', while the second connectors 54A, 54B, 54C, 54D, 56E are mounted to the segments 18A', 18B', 18C', 18D', 18E' of the retraction members 14A', 14B', 14C', 14D', 14E' preferably along a centerline of the segments as shown. Stationary posts (or pulleys) 56A, 56B, 56C, 56D, 56E are disposed in respective slots 58A, 58B, 58C, 58D, 58E in the segments 18A', 18B', 18C', 18D', 18E'. The cables 51A, 51B, 51C, 51D, 51E slide along the pulleys as the ring gear 22' is rotated in the clockwise-direction to thereby pull the segments 18A', 18B', 18C', 18D', 18E' and the corresponding retraction arms 16A', 16B', 16C', 16D', 16E' in the radial direction away from the central axis. The ring gear 22' is driven by rotation of a drive gear 24B and spline 20 in response to user rotation of a knob or arm attached to the spline 20 as described above. In this manner, user rotation of the knob or arm effectuates retraction of retraction arms 16A', 16B', 16C', 16D', 16E' in the radial direction away from the central axis. FIG. 5A illustrates the surgical retraction apparatus in its non-retracted "closed" configuration. In this configuration, the retraction arms form a substantially-closed tube-shaped structure about the central axis 17 similar to that shown in FIG. 2C. FIG. 5B illustrates the surgical retraction apparatus in its fully-retracted "open" configuration. In this configuration, the retraction arms are radially disposed about the central axis 17 to form pieces of a broken tube-shaped structure similar to that shown in FIG. 3C. As is evident, the diameter of the broken-tube shaped structure formed by the retractor arms in the "open" configuration is significantly larger than the diameter of the tube-shaped structure formed by the retractor arms in the "closed" configuration. The retraction arms may be moved radially toward the central axis (and retracted from the fully-retracted "open" position to the "closed" position) by manually applying force to the retraction arms to move them in this radial direction. Such movement pulls the cables 51A, 51B, 51C, 51D, 51E in the radial direction toward the central axis and causes the cables to slide along the stationary posts and rotate the ring gear 22' in the counter-clockwise direction to the "closed" configuration shown in FIG. 5A. The retraction arms may be moved radially toward the central axis (and retracted from the fully-retracted "open" position to the "closed" position) by manually applying force to the retraction arms to move them in this radial direction. Such movement pulls the cables 51A, 51B, 51C, 51D, 51E in the radial direction toward the central axis and causes the cables to slide along the stationary posts and rotate the ring gear 22' in the counter-clockwise direction to the "closed" configuration shown in FIG. 5A.

Figure 6A:
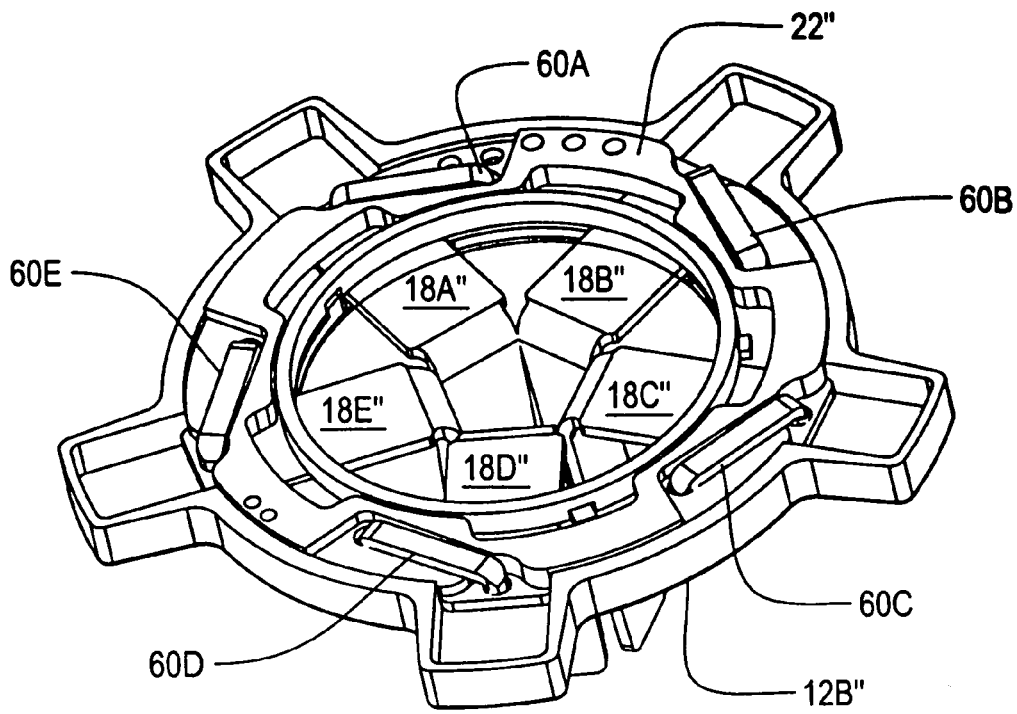
FIGS. 6A and 6B are isometric views illustrating an alternate embodiment of a surgical retraction apparatus according to the present invention wherein radial movement of the retraction members of the surgical retraction apparatus are effectuated with lever mechanisms; the surgical retraction apparatus of FIG. 6A is in its non-retracted "closed" configuration; the surgical retraction apparatus of FIG. 6B is in its fully-retracted "open" configuration.
Figure 6B:
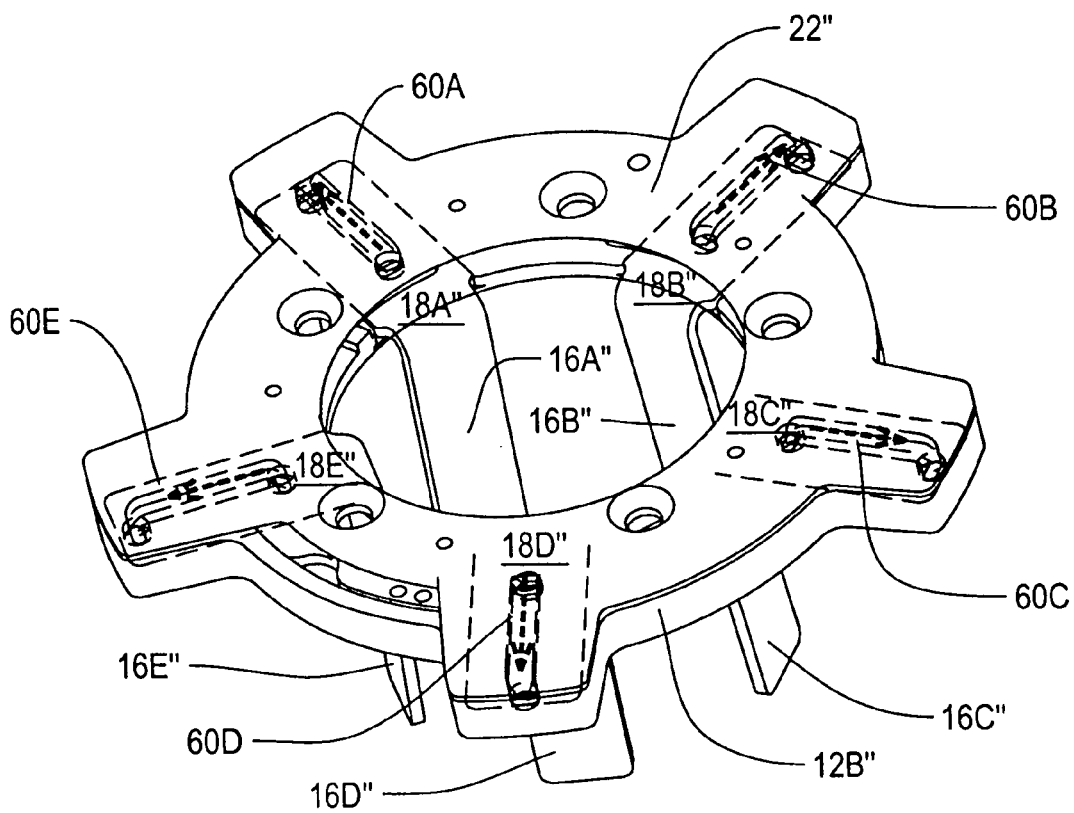

A third embodiment of a surgical retraction apparatus according to the present invention is shown in FIGS. 6A and 6B. In this third embodiment, the rack and pinion interfaces of the apparatus of FIGS. 1-3C are substituted with lever arms mounted within the housing (e.g., housing part 12B"). The lever arms effectuate retraction of the retraction members. As shown, the ends of lever arms 60A, 60B, 60C, 60D, 60E are mounted about the circumference of the sun gear 22" and about the segments 18A", 18B", 18C", 18D", 18E" preferably along a centerline of the segments as shown. The lever arms 60A, 60B, 60C, 60D, 60E rotate as the ring gear 22" is rotated in the counter-clockwise-direction to thereby translate the segments 18A", 18B", 18C", 18D", 18E" and the corresponding retraction arms 16A", 16B", 16C", 16D", 16E" in the radial direction away from the central axis. Similarly, the lever arms 60A, 60B, 60C, 60D, 60E counter-rotate as the ring gear 22" is rotated in the clockwise-direction to thereby translate the segments 18A", 18B", 18C", 18D", 18E" and the corresponding retraction arms 16A", 16B", 16C", 16D", 16E" in the radial direction toward the central axis. The ring gear 22" is driven by rotation of a drive gear and spline in response to user rotation of a knob or arm attached to the spline as described above. In this manner, user rotation of the knob or arm effectuates retraction of retraction arms 16A", 16B", 16C", 16D", 16E" in the radial direction away from (and towards) the central axis. FIG. 6A illustrates the surgical retraction apparatus in its non-retracted "closed" configuration. In this configuration, the retraction arms form a substantially-closed tube-shaped structure about the central axis 17 similar to that shown in FIG. 2C. FIG. 6B illustrates the surgical retraction apparatus in its fully-retracted "open" configuration. In this configuration, the retraction arms are radially disposed about the central axis 17 to form pieces of a broken tube-shaped structure similar to that shown in FIG. 3C. As is evident, the diameter of the broken-tube shaped structure formed by the retractor arms in the "open" configuration is significantly larger than the diameter of the tube-shaped structure formed by the retractor arms in the "closed" configuration.

Figure 8:
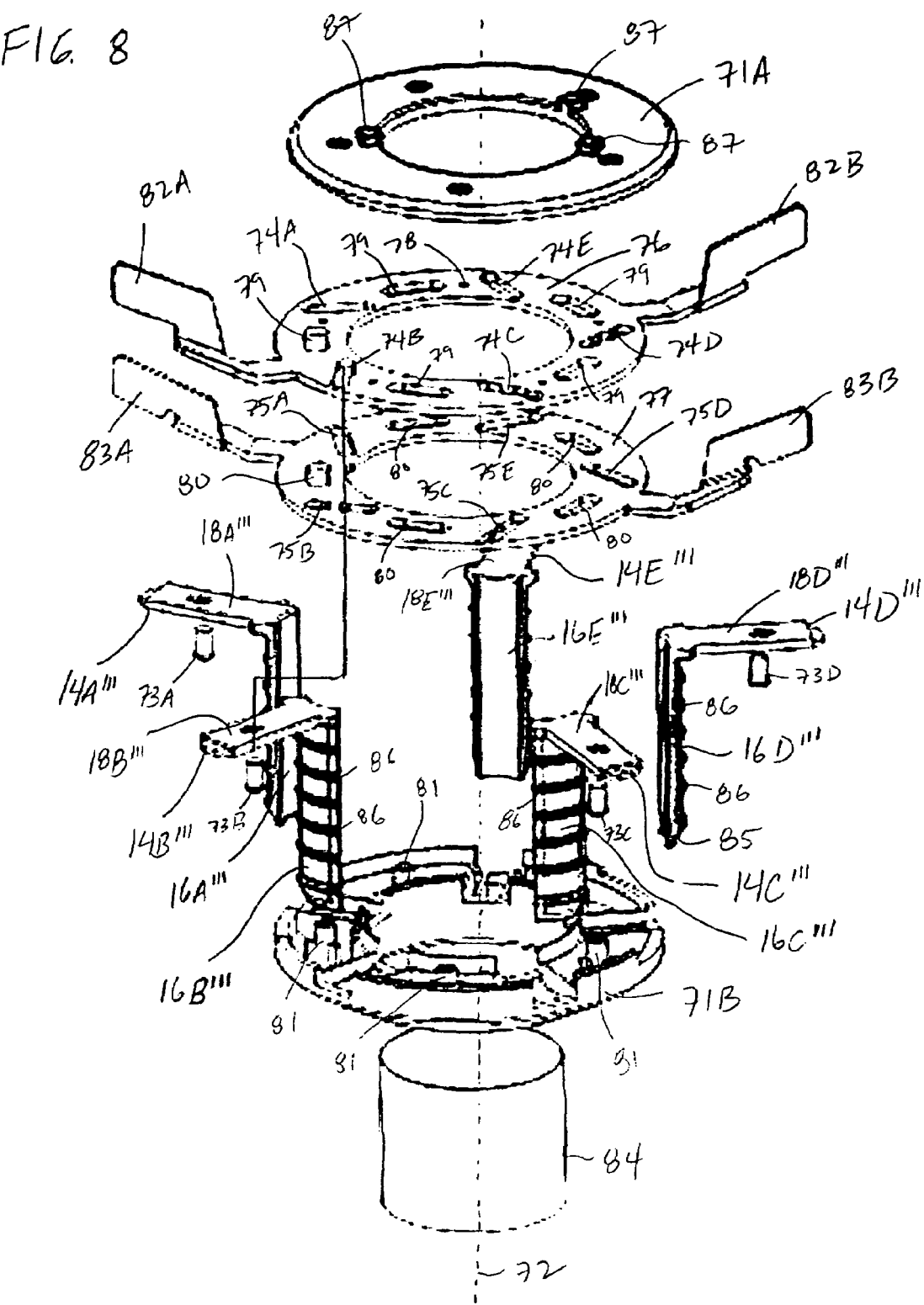
FIG. 8 is an exploded view illustrating an alternate embodiment of a surgical retraction apparatus according to the present invention wherein radial movement of the retraction members are effectuated with slotted plates that rotate relative to one another.
Figure 9:
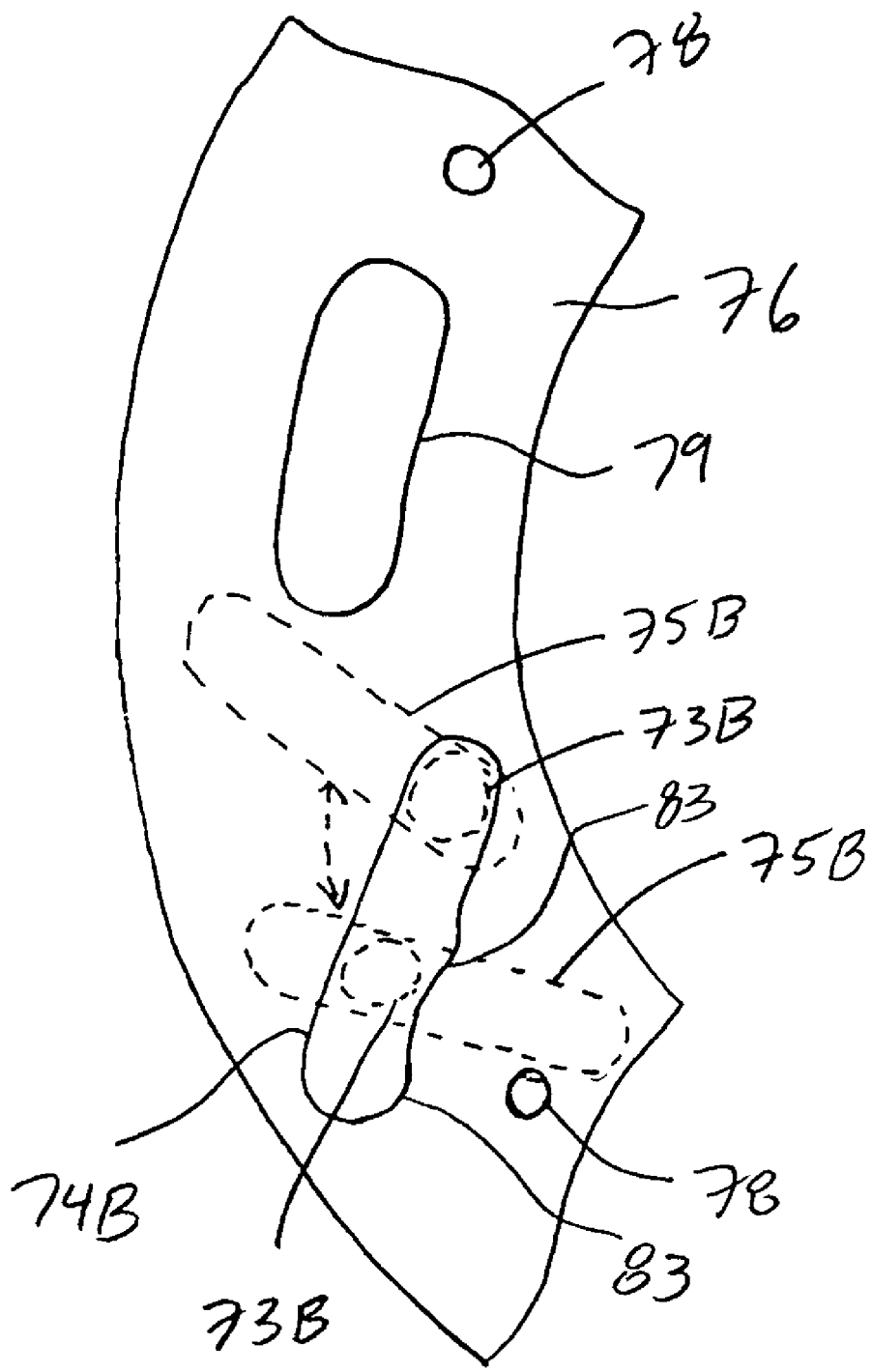
FIG. 9 is a pictorial illustration of the rotation of the slotted plates of FIG. 8 relative to one another, which imparts radial movement of the retraction members.

A fourth embodiment of a surgical retraction apparatus according to the present invention is shown in FIGS. 8 and 9. In this fourth embodiment, the geared interfaces of the apparatus of FIGS. 1-3C are substituted by two plates that are rotatable relative to one another. The plates include cross-angled slot pairs each guiding a cam follower pinion that is affixed a corresponding retraction member. Rotation of the two plates relative to one another translates the cam follower pinions radially within the corresponding cross-angled slot pairs, thereby effectuating retraction of the retraction members. As shown in FIG. 8, the apparatus includes a two-part housing (housing elements 71A, 71B) that supports a plurality of retraction members (for example, the five labeled 14A''', 14B''', 14C''', 14D''' and 14E'''). The retraction members are generally L-shaped, with each having an arm (16A''', 16B''', 16C''', 16D''', 16E''') that projects along a direction substantially parallel to a central axis 72 and a segment (18A''', 18B''', 18C''', 18D''', 18E''') that projects radially outward from its arm. Cam follower pinions 73A, 73B, 73C, 73D, 73E are affixed to the segments 18A''', 18B''', 18C''', 18D''', 18E''' preferably along a centerline of the arms as shown. Each cam follower pinion rides in a corresponding crossed-angle slot pair (labeled 74A, 74B, . . . 74E, 75A, 75B, . . . 75E) in an annular upper plate 76 and an annular lower plate 77 supported within the housing. The upper plate 77 is fixed to the housing by screws that mate to holes 78. The lower plate 77 rests under the bottom of the upper plate 76 and rotates relative to the upper plate 76 through the use of guide slots 79, 80 in the respective plates 76, 77 together with a set of guide pins 81 that extend from the lower plate 77 through corresponding guide slots. A first pair of hand grips 82A, 82B extend from the upper plate 76 beyond the housing. A second pair of hand grips 83A, 83B extend from the lower plate 77 beyond the housing. The hand grips 82A, 82B, 83A, 83B preferably include a molded plastic tab that provides a non-slip gripping surface. The user moves the corresponding hand grips 82A, 83A and/or the corresponding hand grips 82B, 83B apart (or together) to cause rotation of the lower plate 77 relative to the upper plate 76.

As best shown in FIG. 9, rotation of the lower plate 77 relative to the upper plate 76 causes the cam follower pinions 73A, 73B, 73C, 73D, 73E to move in a radial direction (perpendicular to the central axis 72), thereby causing the retraction members 14A''', 14B''', 14C''', 14D''' and 14E''' to move in the radial direction. In this manner, user manipulation of the hand grips effectuates retraction of retraction arms 16A''', 16B''', 16C''', 16D''', 16E''' in the radial direction away from the central axis. The surgical retraction apparatus can be positioned in a non-retracted "closed" configuration, wherein the retraction arms form a substantially-closed tube-shaped structure about the central axis 72 similar to that shown in FIG. 2C. Alternatively, the, surgical retraction apparatus can be positioned in its fully-retracted "open" configuration wherein the retraction arms are radially disposed about the central axis 72 to form pieces of a broken tube-shaped structure similar to that shown in FIG. 3C. As is evident, the diameter of the broken-tube shaped structure formed by the retractor arms in the "open" configuration is significantly larger than the diameter of the tube-shaped structure formed by the retractor arms in the "closed" configuration. The retraction arms may be moved radially toward the central axis (and retracted from the fully-retracted "open" position to the "closed" position) by manually moving the corresponding hand grips 82A, 83A and/or the corresponding hand grips 82B, 83B together.

In the preferred embodiment as best shown in FIG. 9, the slots 74A, 74B, 74C, 74D, 74E in the upper plate 76 include detents 83 that define predetermined points of travel (e.g., the mid-point and terminal-point of travel) of the respective cam follower pinions. The detents 83 provide resistance to the radial movement of the respective cam follower pinions and thus hold the position of the corresponding retraction arms, which allows the user to remove his hands from the hand grips 82A, 82B, 83A, 83B if desired or necessary.

In the illustrative embodiments discussed above, the diameter of the broken-tube shaped structure formed by the retractor arms in the "open" configuration is approximately 40 mm, while the diameter of the tube shaped structure formed by the retractor arms in the "closed" configuration is approximately 12 mm (e.g., to closely accommodate a 10 mm trocar). Other open and closed diameters may be provided, as desired. Although, the provided structure is particularly advantageous in expanding by at least a factor of two or three.

In the illustrative embodiments discussed above, the retraction members are formed of a biocompatible rigid material (such as stainless steel, high strength metal alloys, high strength plastics, a molded plastic exterior on a metal (e.g., steel) structure, or other materials) that provides sufficient strength to bear the loads placed thereon in use during retraction of the body wall. A flexible sleeve (for example, the sleeve 84 of FIG. 8) may be disposed over the retraction arms so that the sleeve encircles the retraction arms. The sleeve forms a continuous surface between the arms that aids in preventing body tissue from entering into the tubular structure formed by the arms during retraction. The sleeve may be formed from a biocompatible latex, silicone elastomer, or a stainless steel cylindrical spring that slips pasts its own surface to provide varying diameter during retraction. In addition, as shown in FIG. 8, the exterior surface of the retraction arms may have a tapered tip 85 to facilitate insertion into the body as well as annular ribs 86 that are spaced apart along the length of the arms to aid in fixation of the retracting arms inside the body. Moreover, the top of the housing (e.g., the top of the housing part 71A) may include a plurality of tabs 87 (for example, three shown) that extend from the housing to provide an anchor point for tying sutures that secure the device to the patient.

Figure 7A:
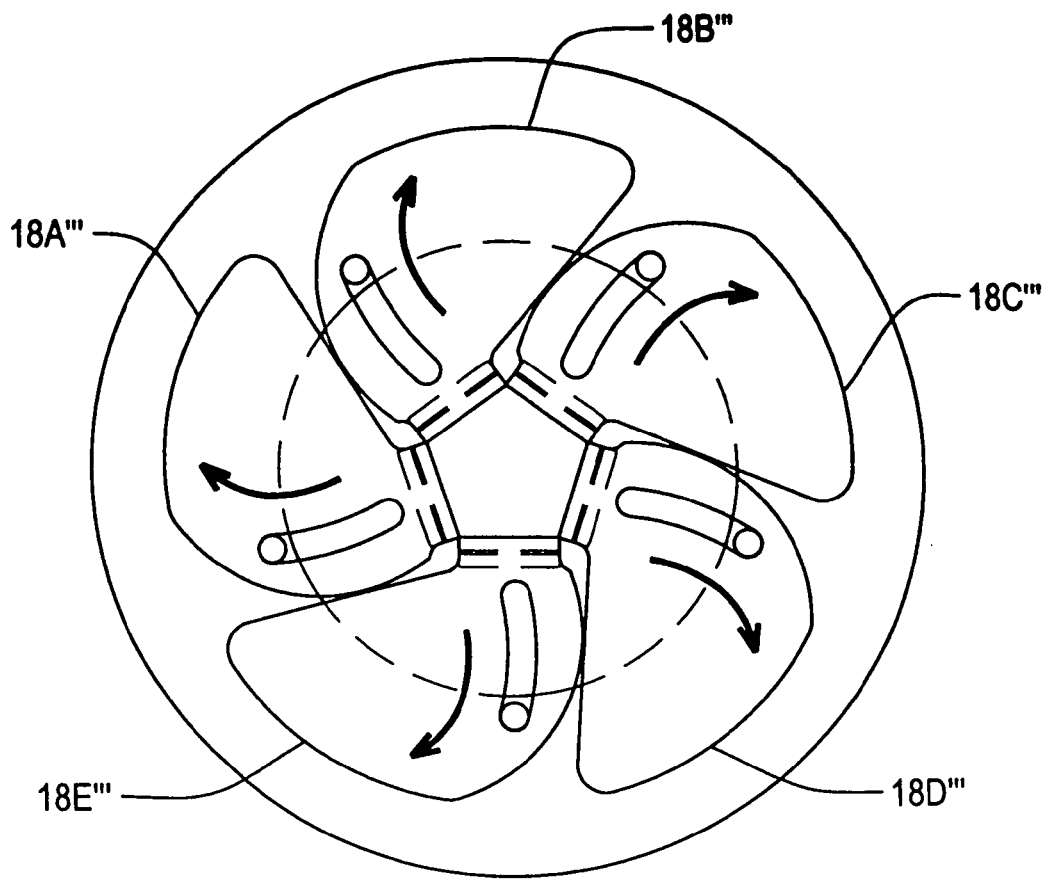
FIGS. 7A and 7B are diagrammatic views illustrating alternate embodiments of surgical retraction apparatus according to the present invention wherein the retraction members are nested about one another in the non-retracted "closed" configuration.
Figure 7B:
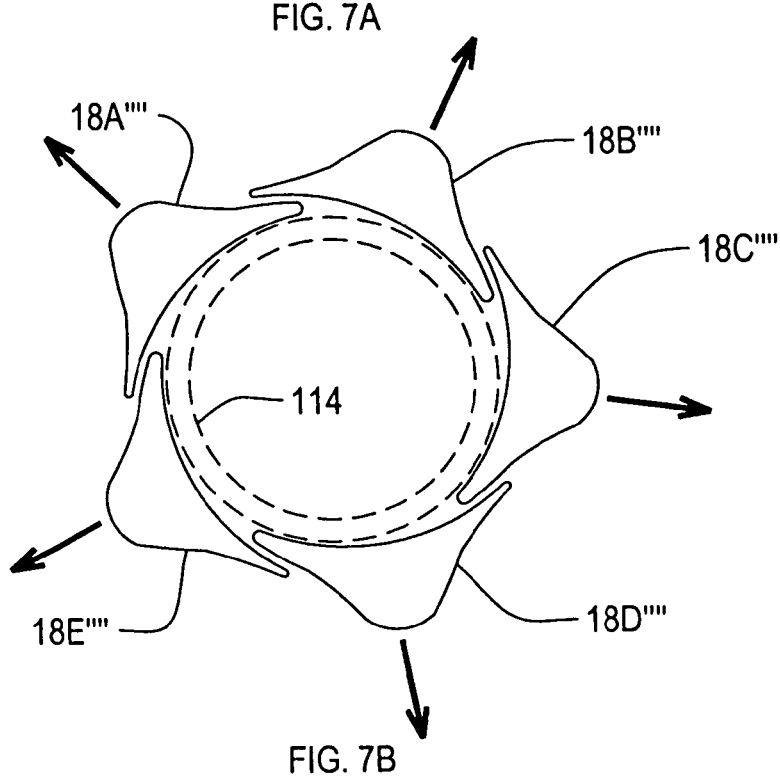

There have been described and illustrated herein an improved surgical retraction apparatus for use in conjunction with a surgical port device. Advantageously, the radial position of the retraction members of the surgical retraction apparatus are easily adjusted to provide a wide range of opening sizes into the body, and thus are effective in retracting the body wall over many different surgical applications. In addition, the surgical retraction apparatus of the present invention is simple to use and effective in conjunction with surgical port devices, and thus is effective in a wide range of laparoscopic and endoscopic procedures. While particular embodiments of the invention have been described, it is not intended that the invention be limited thereto, as it is intended that the invention be as broad in scope as the art will allow and that the specification be read likewise. Therefore, while the elements of the system have been particularly described with respect to their use with particular medical instruments, it may be used with other types of medical instruments. In addition, the surgical retraction apparatus and port devices described herein can be designed and manufactured with different sizes (e.g., varying length and cross-sectional diameter of the components), with different diameters, and with different materials. For example, closed diameters might range from 3 mm to 20 mm or larger, and open diameters might range from 10 mm to 50 mm or larger. Typically, the closed diameter will be between 10 mm and 20 mm and the open diameter will be between 30 mm and 50 mm. Moreover, it is contemplated that other mechanical drive designs, such as ratchet designs or adaptations of the designs described herein, can be used to control the radial retraction motion of the rigid retraction arms of the surgical retraction apparatus. It is also contemplated that the retraction members may be adapted to circumferentially mesh about one another in the closed configuration as shown in FIGS. 7A and 7B. In the configuration of FIG. 7A, the retraction arms are adapted to move relative to one another (e.g., slide, pivot) as well as move radially to effectuate retraction. In the configuration of FIG. 7B, the retraction arms overlap one another. This would enable the circumferential width of the retraction arms to be made larger to better prevent body tissue from entering into the tubular structure formed by the arms during retraction. It will therefore be appreciated by those skilled in the art that yet other modifications could be made to the provided invention without deviating from its spirit and scope as claimed.

What is claimed is:

1. A surgical retraction apparatus for use with a surgical port device having a tubular section that is operably inserted into tissue, the surgical retraction apparatus comprising:

a plurality of rigid retraction members disposed about a central axis that move radially with respect to said central axis between a closed state and an open state, wherein in said closed state said retraction members form a central opening that is adapted to closely fit around the tubular section of the surgical port device, said retraction members being L-shaped, each having an arm that projects along a direction substantially parallel to the central axis and a segment that projects along a directional substantially perpendicular to the central axis; and a plurality of cam follower pinions that are affixed to corresponding segments of said retraction members; and first and second annular plates that are rotatable relative to one another and have cross-angled slot pairs that each guide a corresponding cam follower pinion, wherein rotation of first and second plates relative to one another translates said cam follower pinions radially with respect to said central axis and thus moves said retraction members radially with respect to said central axis, and wherein:

at least one of said first and second annular plates includes means for fixing radial position of said retraction members, said means comprising at least one detent in at least one slot of each cross-angled slot pair.

2. A surgical retraction apparatus according to claim 1, wherein:

said means for fixing radial position of said retraction members comprises first and second detents in at least one slot of each cross-angled slot pair, wherein the first detent defines a mid-point of travel of the corresponding cam follower pinion and the second detent defines a terminal-point of travel of the corresponding cam follower pinion.

* * * * *